(12) United States Patent
Bedell et al.

(10) Patent No.: US 8,828,138 B2
(45) Date of Patent: Sep. 9, 2014

(54) FET NANOPORE SENSOR

(75) Inventors: Stephen W. Bedell, Wappingers Falls, NY (US); Christopher D'Emic, Ossining, NY (US); Hongbo Peng, Hubei (CN); Sufi Zafar, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 1134 days.

(21) Appl. No.: 12/781,514

(22) Filed: May 17, 2010

(65) Prior Publication Data
US 2011/0279125 A1 Nov. 17, 2011

(51) Int. Cl.
*C30B 1/06* (2006.01)
*G01N 27/414* (2006.01)
*B82Y 15/00* (2011.01)

(52) U.S. Cl.
CPC ............ *B82Y 15/00* (2013.01); *G01N 27/4145* (2013.01)
USPC ...................... 117/3; 117/2; 117/86; 438/268

(58) Field of Classification Search
USPC ..................................... 117/2, 3, 86; 438/268
See application file for complete search history.

(56) References Cited

U.S. PATENT DOCUMENTS

| | | |
|---|---|---|
| 5,753,014 A | 5/1998 | Van Rijn |
| 6,503,409 B1 | 1/2003 | Fleming |
| 6,541,353 B1 | 4/2003 | Sandhu et al. |
| 6,579,752 B2 | 6/2003 | De Boer |
| 6,709,929 B2 * | 3/2004 | Zhang et al. .................. 438/268 |
| 6,797,187 B1 | 9/2004 | Galambos et al. |
| 6,827,866 B1 | 12/2004 | Novotny |
| 6,846,702 B1 | 1/2005 | Barth |
| 6,887,391 B1 | 5/2005 | Daneman et al. |
| 7,001,792 B2 | 2/2006 | Sauer et al. |
| 7,052,821 B2 | 5/2006 | Kohl et al. |
| 7,138,672 B2 | 11/2006 | Barth |
| 7,250,115 B2 | 7/2007 | Barth |
| 7,468,271 B2 | 12/2008 | Golovchenko et al. |
| 7,553,730 B2 | 6/2009 | Barth et al. |
| 7,625,706 B2 | 12/2009 | Akeson et al. |

(Continued)

FOREIGN PATENT DOCUMENTS

| | | |
|---|---|---|
| CN | 101203740 A | 6/2008 |
| CN | 101668866 A | 3/2010 |
| WO | 2010020912 A1 | 2/2010 |
| WO | WO2010117470 A2 | 10/2010 |

OTHER PUBLICATIONS

Patolsky et al., Electrical detection of single viruses, PNAS, Sep. 28, 2004, pp. 14017-14022, vol. 101, No. 39, PNAS.org.

(Continued)

*Primary Examiner* — Bob M Kunemund
(74) *Attorney, Agent, or Firm* — Cantor Colburn LLP; Vazken Alexanian

(57) ABSTRACT

A method of using a sensor comprising a field effect transistor (FET) embedded in a nanopore includes placing the sensor in an electrolyte comprising at least one of biomolecules and deoxyribonucleic acid (DNA); placing an electrode in the electrolyte; applying a gate voltage in the sub-threshold regime to the electrode; applying a drain voltage to a drain of the FET; applying a source voltage to a source of the FET; detecting a change in a drain current in the sensor in response to the at least one of biomolecules and DNA passing through the nanopore.

13 Claims, 17 Drawing Sheets

(56) References Cited

U.S. PATENT DOCUMENTS

| | | | |
|---|---|---|---|
| 7,638,345 B2* | 12/2009 | Lee et al. ............ 438/27 |
| 7,678,562 B2 | 3/2010 | Ling |
| 7,765,679 B2 | 8/2010 | Yao et al. |
| 2003/0029839 A1 | 2/2003 | Chou |
| 2003/0104428 A1 | 6/2003 | Branton et al. |
| 2005/0103713 A1 | 5/2005 | Ramsey et al. |
| 2005/0170670 A1 | 8/2005 | King et al. |
| 2006/0154399 A1 | 7/2006 | Sauer et al. |
| 2007/0042366 A1 | 2/2007 | Ling |
| 2007/0178507 A1 | 8/2007 | Wu et al. |
| 2007/0190542 A1 | 8/2007 | Ling et al. |
| 2007/0199341 A1 | 8/2007 | Hart |
| 2008/0121534 A1 | 5/2008 | White et al. |
| 2008/0251877 A1 | 10/2008 | Jain et al. |
| 2008/0254995 A1 | 10/2008 | Kim et al. |
| 2009/0136958 A1 | 5/2009 | Gershow et al. |
| 2010/0026779 A1 | 2/2010 | Yonehara et al. |
| 2010/0127390 A1 | 5/2010 | Barth |
| 2010/0327255 A1 | 12/2010 | Peng et al. |
| 2010/0331194 A1 | 12/2010 | Turner et al. |
| 2011/0033952 A1 | 2/2011 | Khater et al. |
| 2011/0048947 A1 | 3/2011 | Petronis et al. |
| 2011/0279125 A1 | 11/2011 | Bedell et al. |
| 2011/0308949 A1 | 12/2011 | Afzali-Azdakani et al. |

OTHER PUBLICATIONS

Stern et al., Label-free immunodetection with CMOS-compatible semiconducting nanowires, nature Letters, Feb. 2007, pp. 519-522, vol. 445, Nature Publishing Group.

Uram et al., Noise and Bandwidth of Current Recordings from Submicrometer Pores and Nanopores, ACS NANO, 2008, pp. 857-872, vol. 2, No. 5, American Chemical Society.

Kim et al., Rapid Fabrication of Uniformly Sized Nanopores and Nanopore Arrays for Parallel DNA Analysis, Advanced Materials, 2006, pp. 3149-3153, vol. 18, Wiley Inter Science.

Polonsky, et al., "Nanopore in Metal-Dielectric Sandwich for DNA Position Control", Appl. Phys. Lett., vol. 91, 2007, 153103, pp. 153103-1-153103-3.

Branton, et al., "The Potential and Challenges of Nanopore Sequencing," Nature biotechnology 26(10), pp. 1146-1153 (2008).

Bing Dang, "Integrated Thermal-Fluidic I/O Interconnects for an On-Chip Microchannel Heat Sink," IEEE EDL, 27(2), pp. 117-119 (2006).

Heng et al., "Sizing DNA Using a Nanometer-Diameter Pore," Biophysical Journal, vol. 87, Oct. 2004, pp. 2905-2911.

Gunther Zeck, "Noninvasive Neuroelectronic Interfacing with Synaptically connected Snail Neurons Immobilized on a Semiconductor Chip," Neurobiolgy, PNAS, vol. 98, No. 18, pp. 1-6, Aug. 2001.

Meller et al.,"Rapid Nanopore Discrimination Between Single Polynucleotide Molecules," Proc. Natl Acad. Sci. USA, PNAS, vol. 97, No. 3, Feb. 2000, pp. 1079-1084.

Soni G and Meller, "Progress Towards Ultrafast DNA Sequencing Using Solid -State Nanopores," Clinical Chemistry, 53:11, pp. 1996-2001, 2007.

R. Akeson, et al.,"Microsecond Timescale Discrimination Among Polycytidylic Acid, Polyadenylic Acid, and Polyuridylic Acid as Homopolymers or as Segments within Single RNA Molecules," Biophysical Journal, vol. 77, Dec. 1999, pp. 3227-3233.

P. Bergveld, "Thirty Years of Isfetology: What Happened in the past 30 years and what may happen in the next 30 years," MESA, Sensors and Actuatorrs B 88, pp. 1-20, 2003.

Maria Gracheva, et al.,"Simulation of the Electric Response of DNA Translocation Through a Semiconductor Nanopore-capacitor," Nanotechnology 17, pp. 1-13, 2006.

Johnny Ho, "Controlled Nanoscale Doping of Semiconductors Via Molecular Monolayers," Nature Materials, vol. 7, pp. 1-16, Jan. 2008.

Jiali Li, et al., "Ion-beam Sculpting at Nanometre Length Scales," Letter; Nature, vol. 412, pp. 1-4, Jul. 2001.

Johan Lagerqvist, et al., "Fast DNA Sequencing via Transverse Electronic Transport," Nano Letters, vol. 6, No. 4, pp. 1-4, 2006.

International Search Report; International Application No. PCT/US 12/28231; International Filing Date: Mar. 8, 2012; Date of Mailing: Jun. 15, 2012; pp. 1-5.

International Search Report—Written Opinion; International Application No. PCT/US 12/28231; International Filing Date: Mar. 8, 2012; Date of Mailing: Jun. 15, 2012; pp. 1-8.

H. Rucker, "Dopant Diffusion in C-doped Si and SiGe: Physical Model and Experimental Verification," IEEE, IEDM99-345, pp. 1-4, 1999.

A.J. Storm, et al., "Fabrication of Solid-State Nanopores with Single-Nanometre Precision," Nature Materials, Letters, vol. 2, pp. 1-5, Aug. 2003.

Headrick, "Si(100)-(2X1)boron reconstruction: Self-Limiting Monolayer Doping," Appl. Phys. Lett. 57, (26), pp. 1-4, Dec. 1990.

Stefano Vassanelli, et al."Transistor Probes Local Potassium Conductances in the Adhesion Region of Cultured Rat Hippocampal Neurons," The Journal of Neuroscience, Aug. 1999, 19(16); pp. 1-7.

Sufi Zafar, et al, "Optimization of pH Sensing Using Silicon Nanowire Field Effect Transistors with HfO2 as the sensing Surface," Nanotechnology, 22, IOP Publishing, pp. 1-7, 2011.

Chen, et al., "Mechanisms for Formation of a One-Dimensional Horizontal Anodic Aluminum Oxide Nanopore Array on a Si Substrate", J. Electrochem. Soc., vol. 152, No. 12, 2005, pp. D227-D231.

Jayachandran, et al., "Air-Channel Fabrication for Microelectromechanical Systems via Sacrificial Photosensitive Polycarbonates", Journal of Microelectromechanical Systems, vol. 12, No. 2, 2003, pp. 147-159.

Kasianowicz, et al., "Characterization of Individual Polynucleotide Molecules Using a Membrane Channel", Proc. Natl. Acad. Aci. USA, vol. 93, 1996, pp. 13770-13773.

Kim, et al., Rapid Fabrication of Uniformly Sized Nanopores and Nanopore Arrays for Parellel DNA Analysis'', Adv. Mater., vol. 18, 2006, pp. 3149-3153.

Li, et al., "Sacrificial Polymers for Nanofluidic Channels in Biological Applications", Nanotechnology, vol. 14, No. 6, 2003, pp. 578-583.

Chinese Office Action for corresponding Chinese Application No. 201110130886.8, dated Jun. 7, 2013, pp. 1-9.

* cited by examiner

300C

| N-TYPE DRAIN 301C |
| P-TYPE CHANNEL 302C |
| N-TYPE SOURCE 303C |

| P-TYPE DRAIN 301D |
| N-TYPE CHANNEL 302D |
| P-TYPE SOURCE 303D |

| N-TYPE SOURCE 301E |
| --- |
| P-TYPE CHANNEL 302E |
| N-TYPE DRAIN 303E |
| P-TYPE CHANNEL 304E |
| N-TYPE SOURCE 305E |

| P-TYPE SOURCE 301F |
| --- |
| N-TYPE CHANNEL 302F |
| P-TYPE DRAIN 303F |
| N-TYPE CHANNEL 304F |
| P-TYPE SOURCE 305F |

**FORM SILICON MEMBRANE AND CLEAN SILICON MEMBRANE SURFACE;
DEPOSIT SILICON OXIDE LAYER ON TOP SIDE OF MEMBRANE AND ETCH NATIVE OXIDE ON BOTTOM SIDE OF MEMBRANE
801**

**DEPOSIT METAL LAYER AND CAPPING LAYER ON BOTTOM SIDE OF MEMBRANE
802**

**STRIP SILICON OXIDE FROM TOP SIDE OF MEMBRANE; DEPOSIT METAL LAYER AND CAPPING LAYER ON TOP SIDE OF MEMBRANE
803**

**ANNEAL TO FORM TOP AND BOTTOM METAL SILICIDE
804**

**REMOVE TOP AND BOTTOM CAPPING LAYERS AND ANY UNREACTED METAL;
FORM NANOPORE IN FET STACK COMPRISING SILICON MEMBRANE AND TOP AND BOTTOM METAL SILICIDE;
COAT NANOPORE WITH GATE DIELECTRIC
805**

┌─────────────────────────────────────────┐
│  PLACE SENSOR IN ELECTROLYTE            │
│  1401                                   │
└─────────────────────────────────────────┘
                    ⇩
┌─────────────────────────────────────────┐
│  PLACE ELECTRODE IN ELECTROLYTE         │
│  1402                                   │
└─────────────────────────────────────────┘
                    ⇩
┌─────────────────────────────────────────┐
│  APPLY GATE VOLTAGE TO ELECTRODE; APPLY SOURCE, SUB, AND DRAIN VOLTAGES TO SENSOR │
│  1403                                   │
└─────────────────────────────────────────┘
                    ⇩
┌─────────────────────────────────────────┐
│  DNA OR BIOMOLECULES PASS THROUGH SENSOR NANOPORE │
│  1404                                   │
└─────────────────────────────────────────┘
                    ⇩
┌─────────────────────────────────────────┐
│  DETERMINE PRESENCE OF BIOMOLECULES IN ELECTROLYTE AND/OR DNA SEQUENCE FOR BIOMOLECULES IN ELECTROLYTE BASED ON CHANGE IN DRAIN CURRENT IN SENSOR │
│  1405                                   │
└─────────────────────────────────────────┘

FIG. 14

FET NANOPORE SENSOR

FIELD

This disclosure relates generally to the field of field effect transistor based sensors for sequencing deoxyribonucleic acid (DNA) and proteins. The sensors can also be used for detection of biological molecules such as proteins and viruses.

DESCRIPTION OF RELATED ART

Mapping the sequences of bases of a DNA strand is of great importance in life sciences. Since a single base is about 0.7 nanometers (nm) long when the DNA strand is stretched, it is important that a sensor for sequencing has spatial resolution of about 1 nm or less. Fabricating such a sensor is challenging. Another area of great importance in life sciences is detection of proteins and viruses. For protein and viruses detection, a disadvantage of many FET-based sensors is that a sensing surface of the sensor must to be covered with a biological coating that specifically binds the biomolecules to be detected. Applying the appropriate coating may be labor intensive and expensive. Further, the sensor may only be used to detect the particular biomolecules that bind with the coating, limiting the usefulness of the sensor.

A biomolecule sensor may comprise a field effect transistor (FET). However, for protein and viruses detection, a disadvantage of many FET-based sensors is that a sensing surface of the sensor must to be covered with a biological coating that specifically binds the biomolecules to be detected. Applying the appropriate coating may be labor intensive and expensive. Further, the sensor may only be used to detect the particular biomolecules that bind with the coating, limiting the usefulness of the sensor. A FET sensor may comprise highly doped source and drain regions formed by ion implantation followed by high temperature annealing (about 1000° C.). Though this method is standard for forming source and drain regions in longer channel (greater than 10 nm) FET devices, ion implantation and anneal may pose a problem for fabrication of relatively short FET channel (less than about 5 nm) required for high sensitivity FET devices, as ion implantation and high temperature activation annealing produce dopant density profiles in the source/drain regions that may extend several nanometers into the channel region of the FET. Consequently, the sensitivity of a FET sensor formed in this manner may be degraded, making the FET sensor inappropriate for use for sequencing DNA.

SUMMARY

In one aspect, a method of using a sensor comprising a field effect transistor (FET) embedded in a nanopore includes placing the sensor in an electrolyte comprising at least one of biomolecules and deoxyribonucleic acid (DNA); placing an electrode in the electrolyte; applying a gate voltage in the sub-threshold regime to the electrode; applying a drain voltage to a drain of the FET; applying a source voltage to a source of the FET; detecting a change in a drain current in the sensor in response to the at least one of biomolecules and DNA passing through the nanopore.

In one aspect, a method of forming a sensor comprising a field effect transistor (FET) sensor embedded in a nanopore includes epitaxially growing a FET stack comprising a source layer, a drain layer, and a channel layer on a silicon on insulator (SOI) wafer; forming a top silicon nitride layer over the FET stack; forming a bottom silicon nitride layer under the SOI wafer; forming a window in the bottom silicon nitride and the SOI wafer; forming a nanopore in the FET stack; and coating the nanopore with a gate dielectric to form the FET sensor.

In one aspect, a method of forming a sensor comprising a field effect transistor (FET) sensor embedded in a nanopore includes forming a silicon membrane; forming an oxide layer on the silicon membrane; forming a first metal layer on a side of the silicon membrane opposite the oxide layer, and a first capping layer over of the first metal layer; removing the oxide layer; forming a second metal layer on a side of the silicon membrane opposite the first metal layer, and a second capping layer over of the second metal layer; annealing the silicon membrane and first and second metal layers to form first and second metal silicide layers on opposite sides of the silicon membrane; removing the first and second capping layers; forming a nanopore through the silicon membrane and the first and second metal silicide layers; and coating the nanopore with a gate dielectric to form the FET sensor.

Additional features are realized through the techniques of the present exemplary embodiment. Other embodiments are described in detail herein and are considered a part of what is claimed. For a better understanding of the features of the exemplary embodiment, refer to the description and to the drawings.

BRIEF DESCRIPTION OF THE SEVERAL VIEWS OF THE DRAWINGS

Referring now to the drawings wherein like elements are numbered alike in the several FIGURES:

FIGS. 3A-F illustrate embodiments of a FET stack.

FIG. 8 illustrates an embodiment of a method of forming a FET nanopore sensor comprising a metal silicide source/drain FET stack.

FIG. 14 illustrates an embodiment of a method of operating a FET nanopore sensor.

DETAILED DESCRIPTION

Embodiments of systems and methods for a FET nanopore sensor are provided, with exemplary embodiments being discussed below in detail. A FET nanopore sensor may be used to detect various types of biomolecules without requiring a sensing surface covered with a biological coating to bind the biomolecules. A FET nanopore sensor may also be used to sequence DNA strands. The FET nanopore sensor may have a relatively short channel length (less than about 3 nm in some embodiments, and less than about 1 nm in some preferred embodiments), so that the sensitivity of the FET nanopore sensor is appropriate for sequencing DNA. The FET nanopore sensor may be fabricated in a manner that results in abrupt junctions between highly doped source and drain regions that are separated by a relatively thin channel region.

The FET nanopore sensor may comprise a FET stack with a nanopore located in the FET stack. The FET stack comprises a channel region located in between a source and a drain region. The channel region may have a doping type (p-type or n-type) that is opposite a doping type (p-type or n-type) of the source and drain regions. To form abrupt junctions between the source/drain regions and the channel region, the diffusion of dopant atoms between the source/drain regions and the channel region may be minimized during the fabrication process by using epitaxial growth on a silicon-on-insulator (SOI) substrate to form the FET stack. Epitaxial growth is performed at a relatively low temperature (less than about 600° C.), which reduces the diffusion of dopant atoms. Layers of materials including but not limited to silicon germanium (SiGe), carbon-doped silicon germanium (SiGe:C), or silicon carbide (SiC) may be formed to act as barriers to diffusion of dopant atoms during fabrication of the FET nanopore sensor. Alternately, the FET stack may comprise a silicon channel between a metal silicide source and drain.

Figure 1:
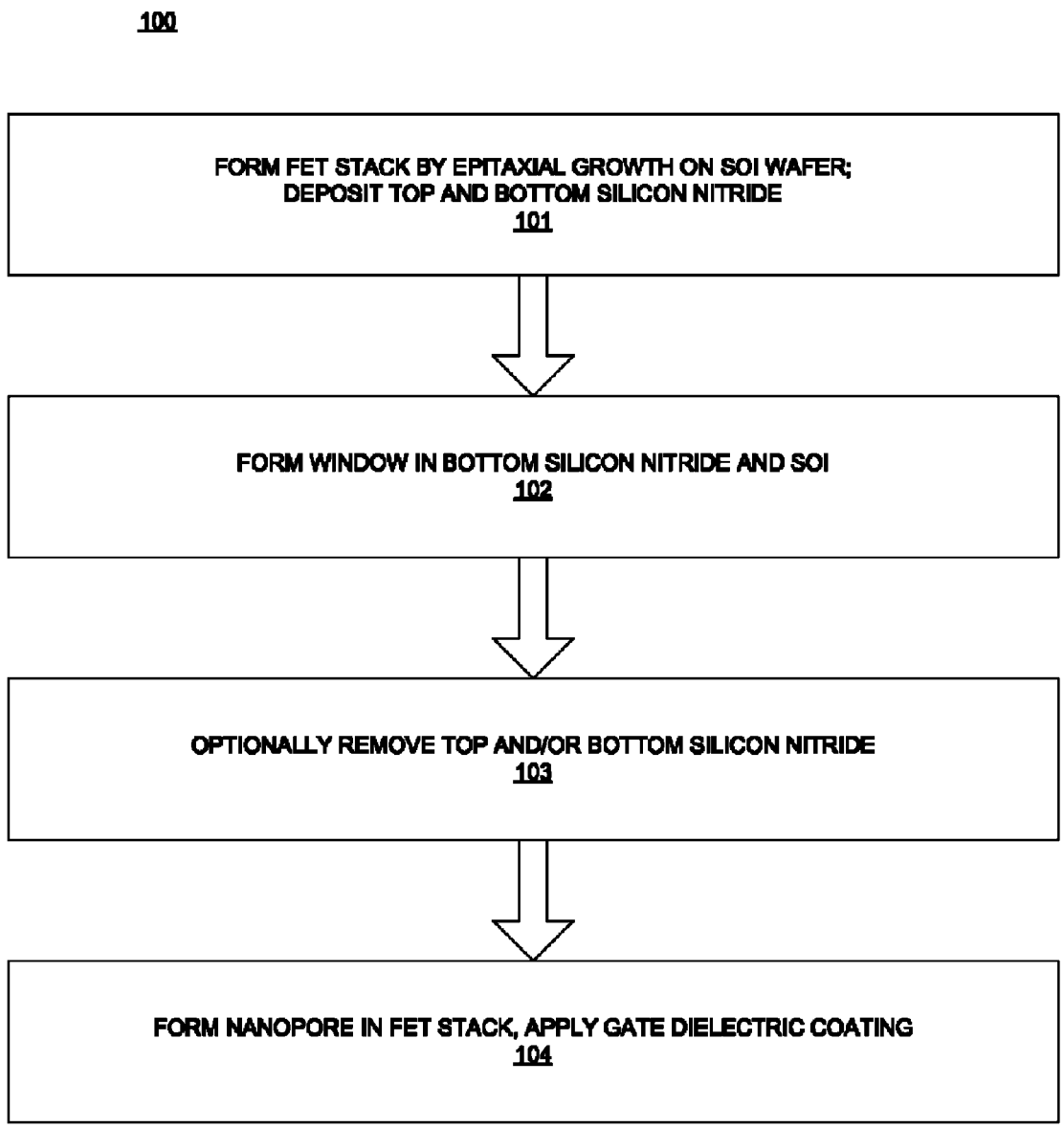
FIG. 1 illustrates an embodiment of a method of forming a FET nanopore sensor.
Figure 2:
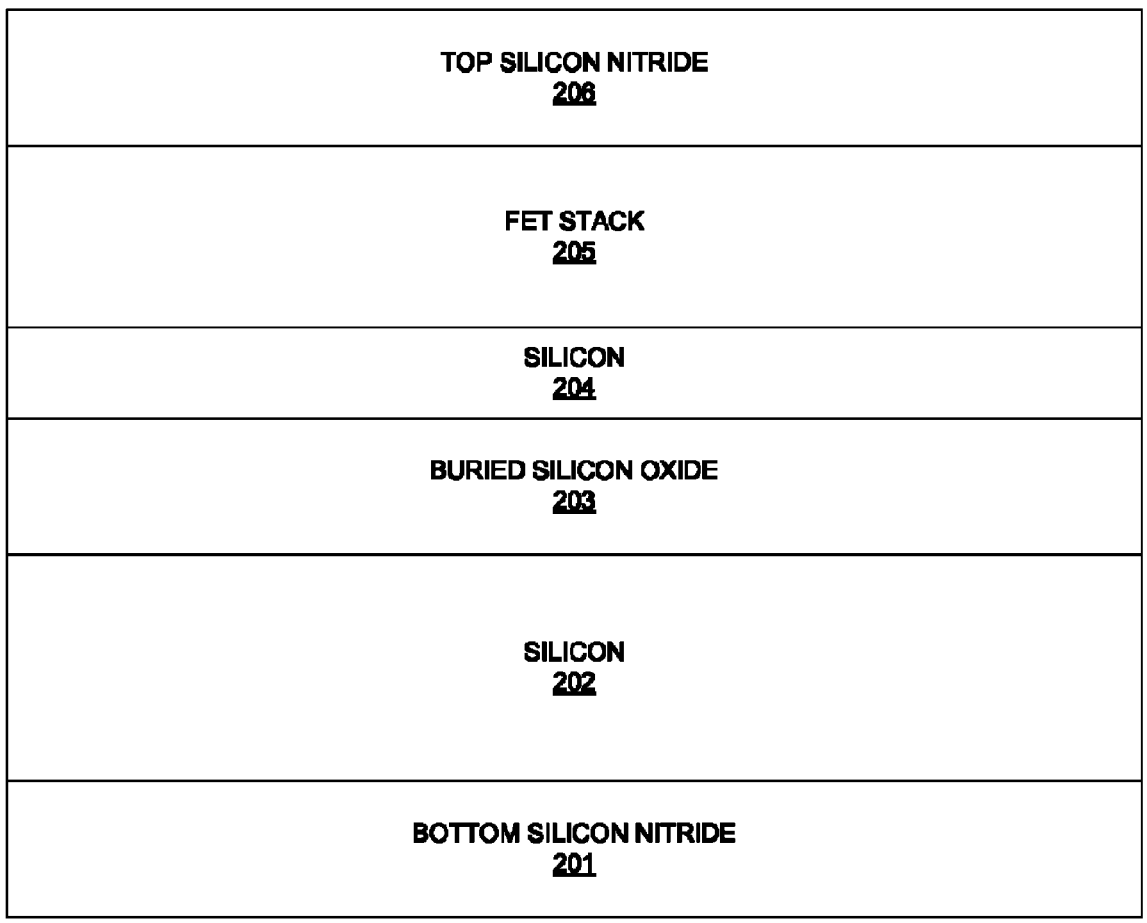
FIG. 2 illustrates an embodiment of a FET stack grown on a silicon-on-insulator (SOI) wafer after deposition of silicon nitride.

FIG. 1 illustrates an embodiment of a method 100 of making a FET nanopore sensor. FIG. 1 is discussed with respect to FIGS. 2-7. In block 101, a FET stack 205 is epitaxially grown on a SOI wafer (comprising a relatively thick silicon layer 202, buried silicon oxide layer 203, and top silicon layer 204), as is shown in FIG. 2. Various methods of forming FET stack 205 are discussed below in further detail with respect to FIGS. 3A-F. Top silicon nitride layer 206 and bottom silicon nitride layer 201 are formed on FET stack 205 and under silicon layer 202, respectively.

Figure 3A:
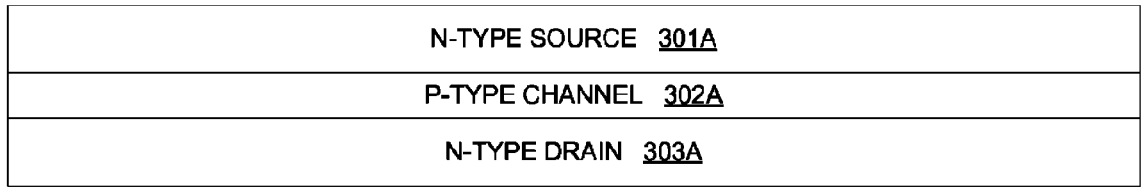

FIGS. 3A-F illustrate embodiments of FET stacks 300A-F that may comprise FET stack 205 of FIG. 2. FET stack 300A shown in FIG. 3A comprises an nFET comprising a drain layer 303A comprising heavily doped n-type silicon, under a channel layer 302A comprising lightly doped p-typed SiGe or SiC doped with boron, under a source layer 301A comprising heavily doped n-type silicon. The drain layer 303A is first epitaxially grown on silicon layer 204 (of FIG. 2), then channel layer 302A is epitaxially grown on drain layer 303A, and source layer 301A is epitaxially grown on channel layer 302A. Channel layer 302A comprises abrupt junctions with both source layer 301A and drain layer 303A. Channel layer 302A may have a thickness of less than 3 nm in some embodiments, and less than 1 nm in some preferred embodiments. Source layer 301A is formed over the channel layer 302A in such a manner that minimizes n-type dopant diffusion from n-type source layer 301A into p-type channel region 302A. Additionally, as shown in FIG. 3C, an nFET stack 300C comprising an n-type drain 301C, n-type source 303C, and p-type channel 302C may also be formed in a manner similar to pFET stack 300A, with the source on the bottom and the drain on the top.

In some embodiments, a boron-doped channel layer 302A may be formed by the epitaxial growth of a layer of p-type material on an existing n-type drain layer 303A; drain layer 303A may be formed using a chemical vapor deposition (CVD) process. The wafer may be pre-baked in a purified hydrogen (H2) ambient at a temperature greater than about 750° C., and more typically greater than about 850° C. The temperature may then be lowered to about 650° C. or less; for monolayer level growth and doping control, temperatures below about 550° C. are preferred. The dopant gas may comprise diborane (B2H6) and the semiconductor precursors may comprise silane, disilane, trisilane, germane, or any combination thereof. In other embodiments, combinations of intrinsic (undoped) multilayer growth and boron exposure may be used to form p-type channel layer 302A. To preserve the boron doping concentration at the monolayer level, channel layer 302A may be grown using a material in which boron has a relatively low diffusivity, such as Si alloyed with Ge or C (or mixtures thereof). Ge content in channel layer 302A may be adjusted to tune the threshold voltage of the FET nanopore sensor. The subsequent growth of the n-type source layer 301A on channel layer 302A may be performed at as low a temperature as possible. Growth of source layer 301A may be preformed using phosphine or arsine as dopant gases and silane, disilane, trisilane, any chlorosilane, or germane (or mixtures thereof) as the semiconductor precursors. Preferably, the use of low-temperature growth using higher-order silanes (di- and tri-silanes) allows the source region 301A to be grown at temperature below about 600° C.

Figure 3B:
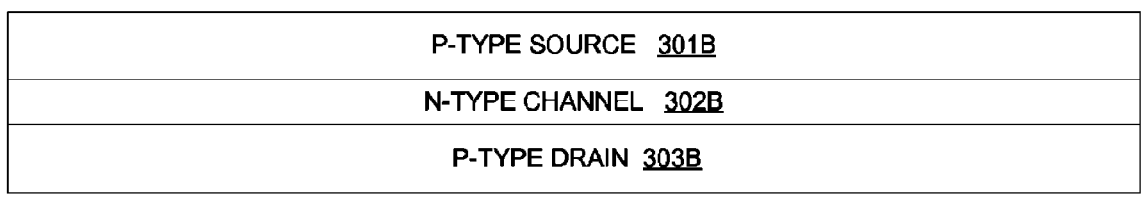

FET stack 300B shown in FIG. 3B comprises a pFET comprising a heavily doped p-type drain layer 303B, on a channel layer 302B comprising n-doped Si, on a heavily doped p-type source layer 301B. The drain layer 303B is first epitaxially grown on silicon on insulator (SOI) of FIG. 2, then channel layer 302B is epitaxially grown on drain layer 303B, and source layer 301B is epitaxially grown on channel layer 302B. The formation of channel region 302B and the subsequent formation of source layer 301B may be performed at relatively low temperature, less than about 600° C. to limit diffusive broadening of the abrupt profile. Source and drain layers 301B and 303B may be doped with boron in some embodiments. The source layer 301B and drain layer 303B may comprise p-type SiGe, SiGe:C or SiC in some embodiments, which may act to reduce boron diffusion into channel layer 302B. Channel layer 302B comprises abrupt junctions with both source layer 301A and drain layer 303B. Channel layer 302B may have a thickness of less than 3 nm in some embodiments, and less than 1 nm in some preferred embodiments. Additionally, as shown in FIG. 3D, a pFET stack 300D comprising an p-type drain 301D, p-type source 303D, and n-type channel 302D may also be formed in a manner similar to pFET stack 300B, with the source on the bottom and the drain on the top.

Boron diffusion into channel layer 302B may also be limited by formation of source/drain cladding layers adjacent to channel layer 302B to contain the boron from source layer 301B and drain layer 303B. For example, before growth of channel region 302B, a cladding layer of SiGe, SiGe:C, or SiC layer may be grown at a relatively low temperature on drain layer 303B before formation of channel layer 302B, which may limit the diffusivity of the boron from drain layer 303B. A second cladding layer may then be formed on channel region 302B before formation of source layer 301B.

Channel layer 302B may comprise silicon doped n-type dopants such as phosphorus or arsenic, which have relatively low diffusivity. Channel layer 302A may be formed by growing a layer of undoped silicon on drain layer 303B, and then growing source layer 301B on undoped channel layer 302B. The FET stack 300B may then be exposed to the n-type dopants through methods including but not limited to ion implantation, channeled implant, gas-phase diffusion, or other ex-situ methods of inserting n-type dopants. Diffusion of n-type dopants is greater in SiGe alloys than in Si, therefore, the n-type dopants may be transported to the channel layer 302B through source layer 301B at a relatively low temperature to maintain the boron abruptness in the FET stack 300B. Any n-type dopants that diffuse into in the source layer 301B and drain layer 303B are insignificant, as source layer 301B and drain layer 303B are already degenerately doped with boron.

In other embodiments, the FET stack 205 may comprise dual FETs, as are shown in FIGS. 3E-F. FIG. 3E illustrates a dual nFET stack 300E, comprising an n-type source 301E over a p-type channel 302E over a n-type drain 303E over a second p-type channel 304E over an n-type source 305E. Channel regions 302E and 304E may have the same channel length; the channel length may be less than about 1 nm in some embodiments. FIG. 3F illustrates a dual pFET stack 300F, comprising a p-type source 301F over a n-type channel 302F over a p-type drain 303F over a second n-type channel 304F over an p-type source 305F. Channel regions 302F and 304F may have the same channel length; the channel length may be less than about 1 nm in some embodiments.

Figure 4:
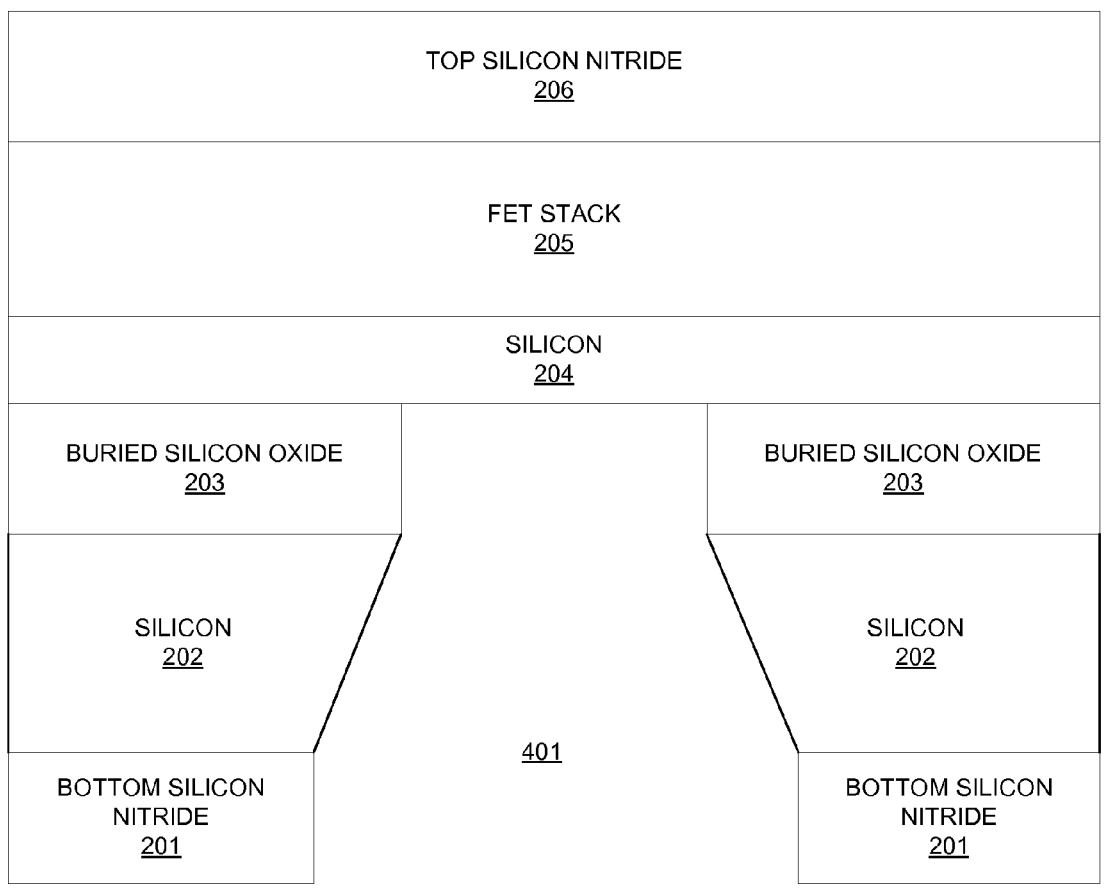
FIG. 4 illustrates an embodiment of the device of FIG. 2 after formation of a window in the bottom silicon nitride, silicon, and buried silicon oxide layers.
Figure 6:
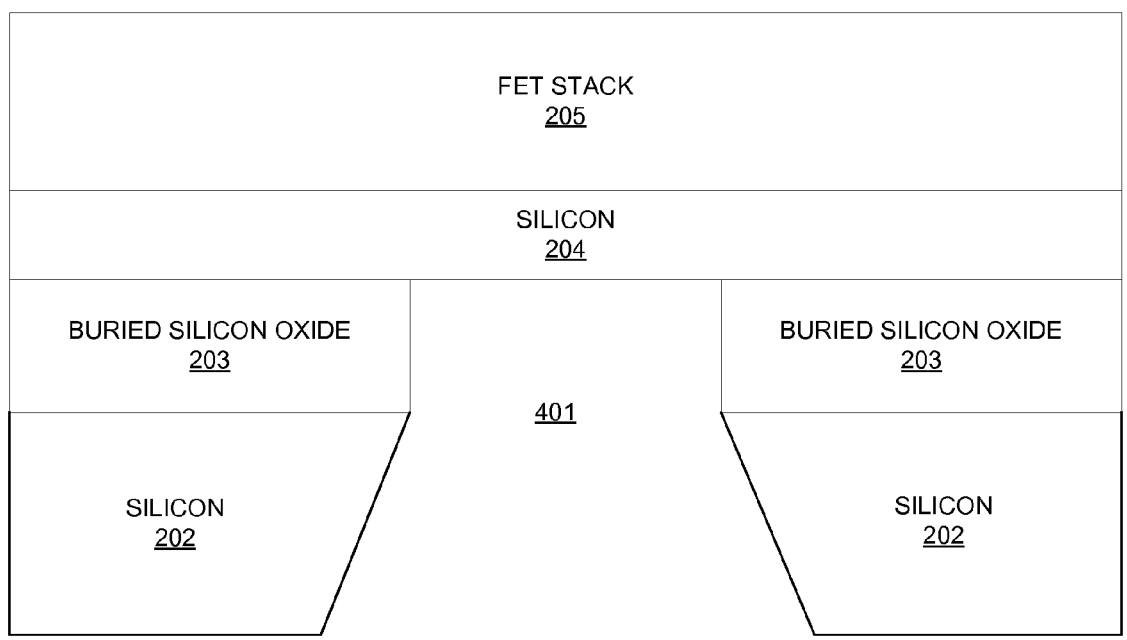
FIG. 6 illustrates an embodiment of the device of FIG. 4 after removal of the silicon nitride.

Returning to FIG. 1, in block 102, photolithography and reactive ion etching are performed on bottom silicon nitride 201, then silicon layer 202 and buried silicon oxide layer 203 are etched to form window 401 as is shown in FIG. 4. Etching may comprise use of a potassium hydroxide (KOH) or a Tetramethylammonium hydroxide (TMAH) solution at 80° C. In block 103, bottom silicon nitride 201 and/or top silicon nitride 206 may be optionally removed using reactive ion etching, as is shown in FIG. 6.

Figure 5:
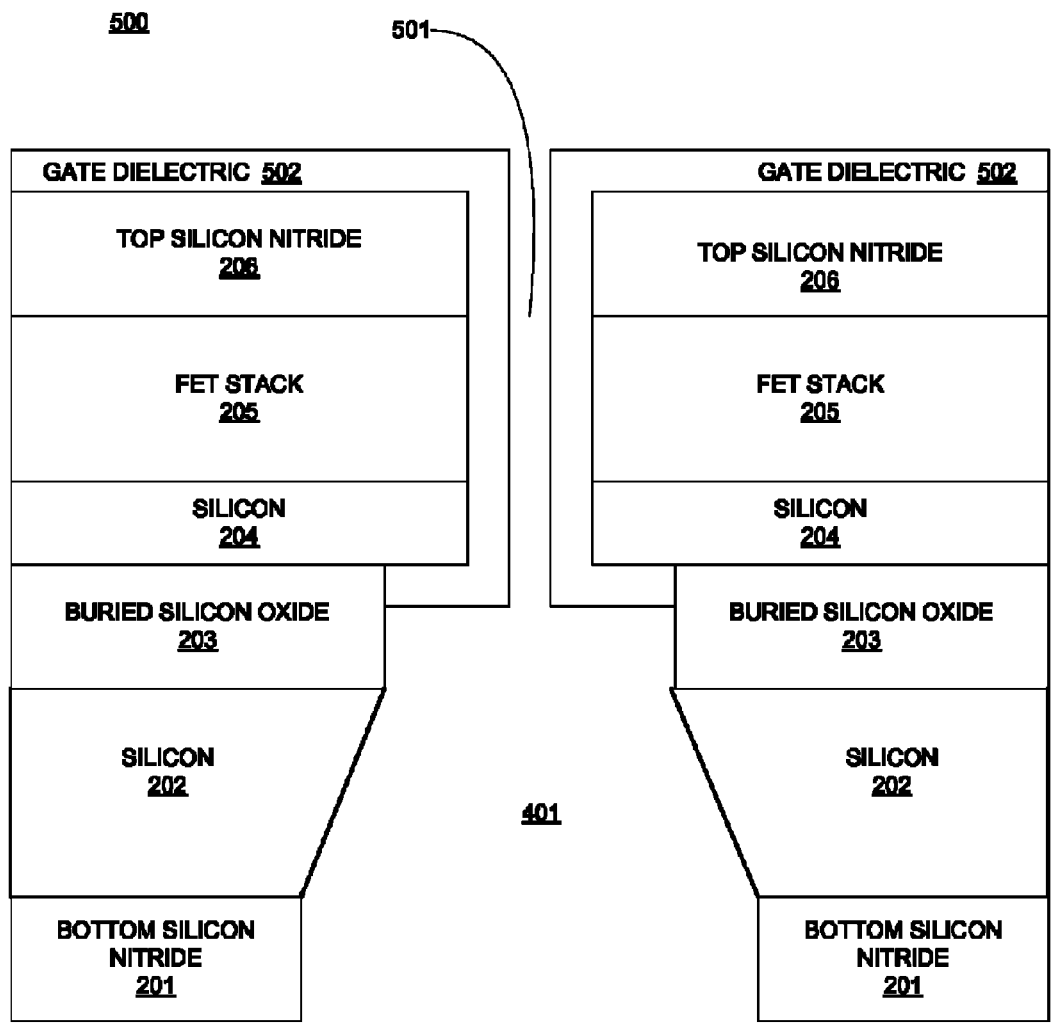
FIG. 5 illustrates an embodiment of the device of FIG. 4 after formation of a nanopore in the FET stack and gate dielectric layer.
Figure 7:
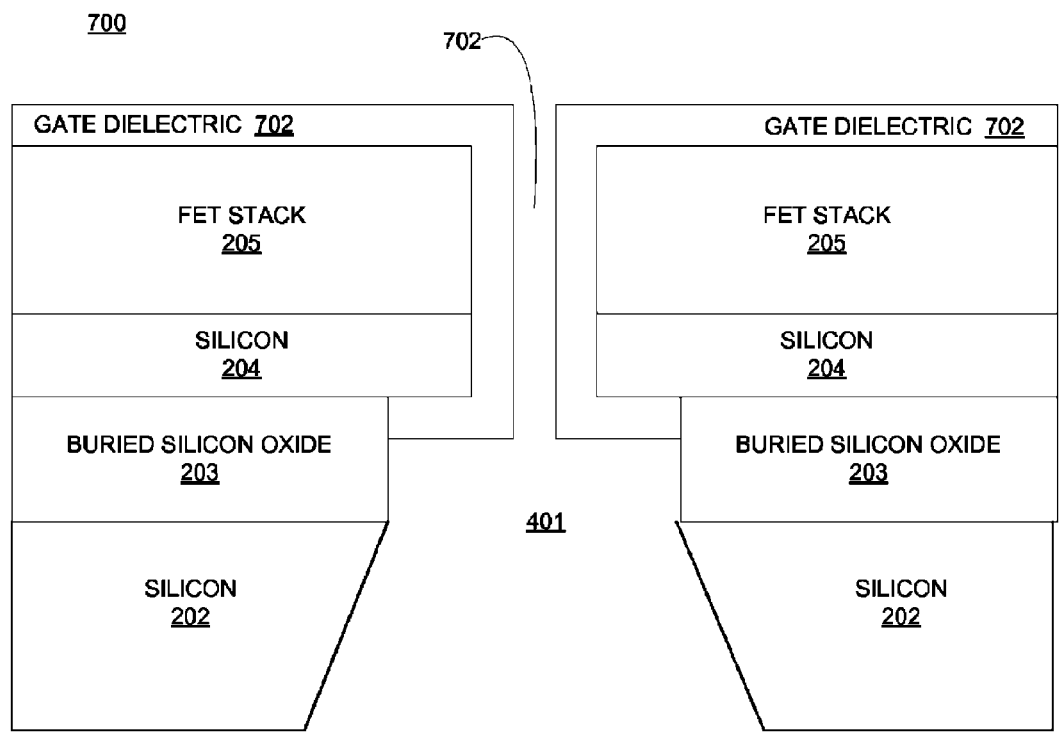
FIG. 7 illustrates an embodiment of the device of FIG. 6 after formation of a nanopore in the FET stack and gate dielectric layer.

In block 104, a nanopore (501, 701) is formed in FET stack 205 and silicon 204, as is shown in FIGS. 5 and 7. In the embodiment of FIG. 5, top silicon nitride 206 is present, and the nanopore 501 is formed in FET stack 205, silicon 204, and top silicon nitride 206. In the embodiment of FIG. 7, top silicon nitride 206 has been removed (as shown in FIG. 6), and the nanopore is formed in FET stack 205 and silicon 204. Nanopore (501, 701) may be sized according to the type of biomolecules or DNA the sensor is used to detect in some embodiments. The gate dielectric layer (502, 702) is then formed to coat the surface of the nanopore (501, 701). Gate dielectric layer (502, 702) may comprise a high-k oxide material in some embodiments, and may comprise a bilayer of SiO2/HfO2 in some embodiments. The gate dielectric layer (502, 702) may be formed by atomic layer deposition (ALD) in some embodiments.

Figure 9:
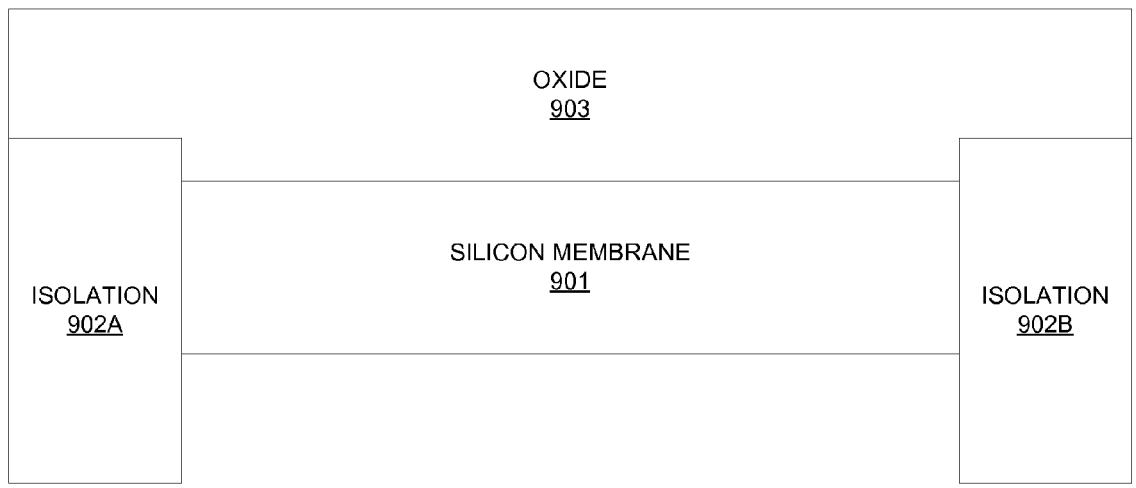
FIG. 9 illustrates an embodiment of a silicon membrane with an oxide layer.

FIG. 8 illustrates an embodiment of a method 800 for forming a FET nanopore sensor comprising a metal silicide source and drain. FIG. 8 is discussed with respect to FIGS. 9-13. In block 801, a silicon membrane 901 is formed between isolation regions 902A-B, as shown in FIG. 9. The top and bottom surfaces of silicon membrane 901 may be cleaned using SC1 or SC2-based chemistry without use of megasonics, to preserve the integrity of silicon membrane 901. In some embodiments, the cleaning may comprise a 10 part per million (ppm) O3/Di water+1:1:40 NH4OH:H2O2:H2O, at 35° C., for 5 minutes, followed by 1:100 HCl:Di water, at 60° C., for 5 minutes. A silicon oxide layer 903 is then formed on the top side of the cleaned silicon membrane 901. Silicon oxide layer 903 may be formed at a relatively low temperature. After formation of silicon oxide layer 903, any native oxide located on the bottom side of silicon membrane 903 is etched using, for example, hydrofluoric acid.

Figure 10:
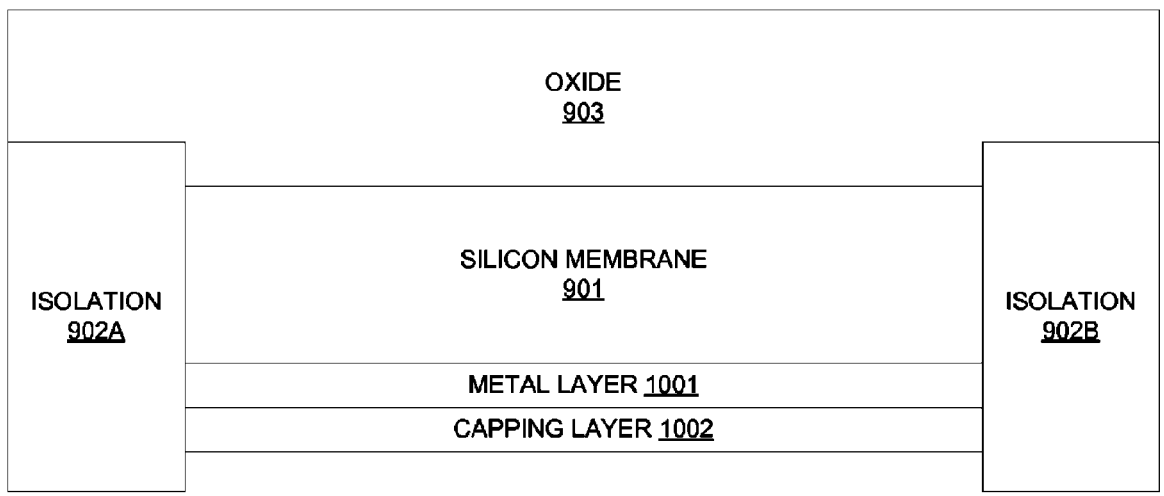
FIG. 10 illustrates an embodiment of the device of FIG. 9 after formation of a metal layer and a capping layer.
Figure 11:
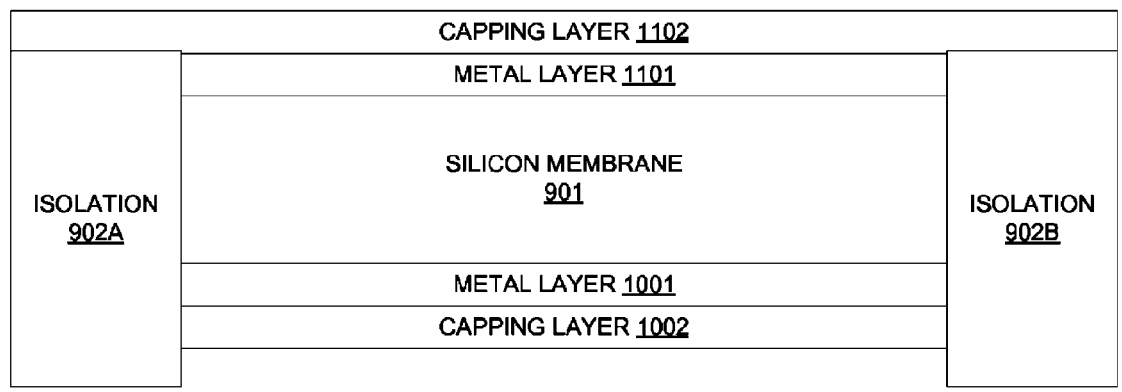
FIG. 11 illustrates an embodiment of the device of FIG. 10 after removal of the oxide layer and formation of a second metal layer and a second capping layer.

In block 802, a metal layer 1001 and a capping layer 1002 are formed on the bottom side of silicon membrane 901, as shown in FIG. 10. Metal layer 1001 may comprise platinum (Pt), nickel (Ni), cobalt (Co), titanium (Ti), erbium (Er), ytterbium (Yb) or nickel platinum (NiPt) in some embodiments. Capping layer 1002 may comprise titanium nitride (TiN), or tungsten (W) in some embodiments, and may have a thickness of about 15 nm. In block 803, silicon oxide layer 903 is removed, as shown in FIG. 11. Silicon oxide layer 903 may be removed using hydrofluoric acid in some embodiments. Metal layer 1101 and capping layer 1102 are then formed on the top side of silicon membrane 901. Metal layer 1101 may comprise platinum (Pt), nickel (Ni), cobalt (Co), titanium (Ti), or nickel platinum (NiPt) in some embodiments. Capping layer 1102 may comprise titanium nitride (TiN), or tungsten (W) in some embodiments, and may have a thickness of about 15 nm.

Figure 12:
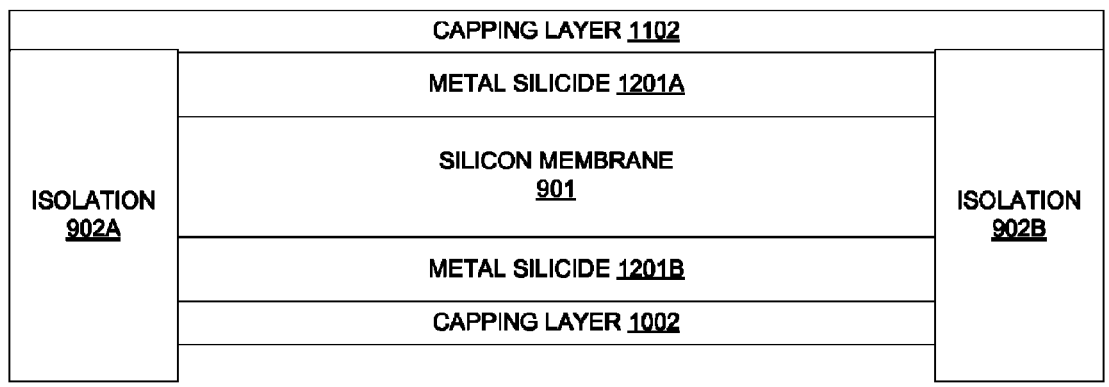
FIG. 12 illustrates an embodiment of the device of FIG. 11 after annealing to form silicide.
Figure 13:
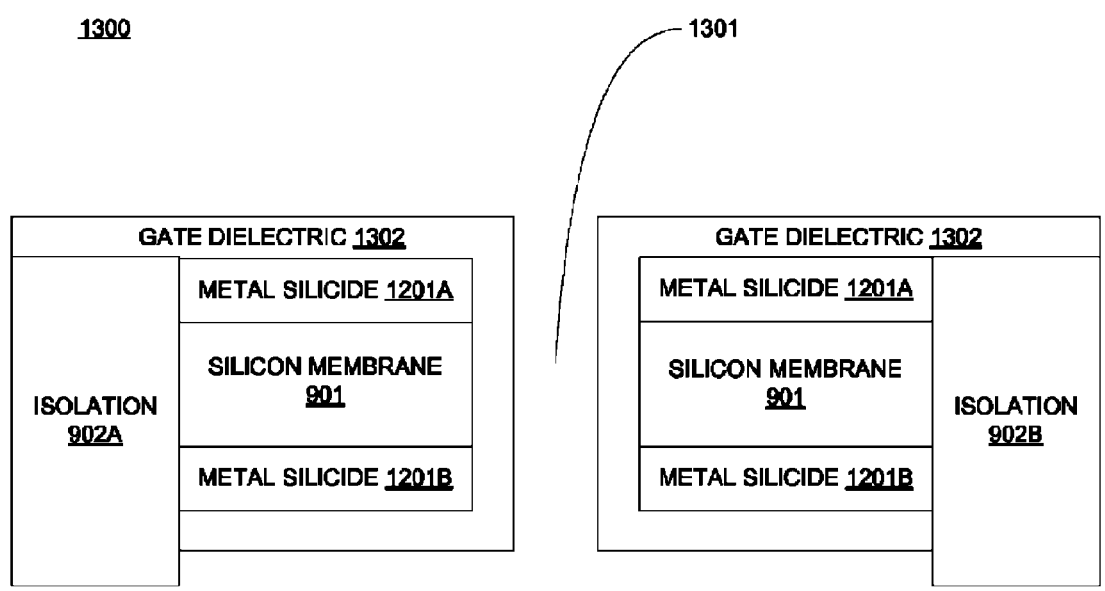
FIG. 13 illustrates an embodiment of the device of FIG. 12 after removal of the capping layers, formation of a nanopore, and formation of the gate dielectric.

In block 804, the device 1100 of FIG. 11 is annealed to form metal silicide layers 1201A-B, as shown in FIG. 12. Portions of silicon membrane 901 react with metal layers 1001 and 1101 to form metal silicide layers 1201A-B. The annealing may comprise rapid thermal annealing, or furnace annealing in some embodiments. In block 805, capping layers 1002 and 1102 are removed, as shown in FIG. 13. Capping layers 1002 and 1102 may be removed by wet etching using, for example, a mixture of sulphuric acid and hydrogen peroxide, or aqua regia. Any unreacted portions of metal layers 1001 and 1101 that may be present on metal silicide layers 1201A-B are also removed. Then, a nanopore 1301 is formed in the FET stack comprising metal silicide layers 1201A-B and silicon membrane 901. Nanopore 1301 may be sized according to the type of biomolecules or DNA the sensor is used to detect in some embodiments. Metal silicide layer 1201A comprises the FET source, silicon membrane 901 comprises the FET channel, and metal silicide layer 1201B comprises the FET drain. The gate dielectric layer 1302 is then formed to coat the surface of the nanopore 1301. Gate dielectric layer 1302 may comprise a silicon dioxide or high-k oxide material in some embodiments, and may comprise a bilayer of SiO2/HfO2 in some embodiments. The gate dielectric layer 1302 may be formed by atomic layer deposition (ALD) in some embodiments.

Figure 15:
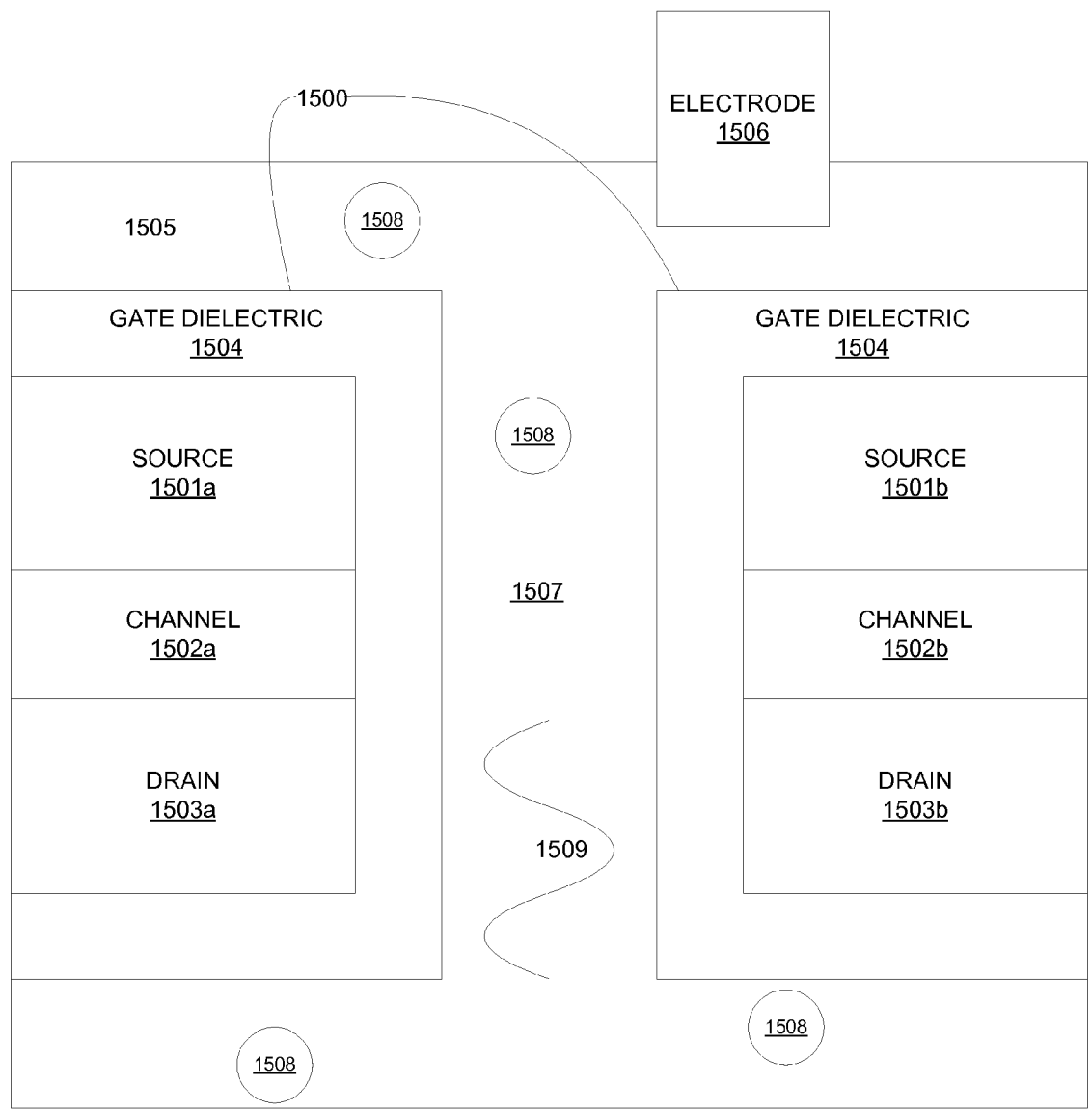
FIG. 15 illustrates an embodiment of a FET nanopore sensor immersed in an electrolyte.

FIG. 14 illustrates an embodiment of a method 1400 of operating a nanopore FET sensor. FIG. 14 is discussed with respect to FIG. 15. In block 1401, sensor 1500 is placed in electrolyte 1505. Electrolyte 1505 may contain one or more DNA strands 1509, and/or biomolecules 1508. Sensor 1500 comprises nanopore 1507 through source 1501$a$-$b$, channel 1502$a$-$b$, and drain 1503$a$-$b$, surrounded by gate dielectric 1504. Channel 1502$a$-$b$ may have a channel length of less than about 3 nm in some embodiments, and less than about 1 nm in some preferred embodiments. Source 1501$a$-$b$, channel 1502$a$-$b$, and drain 1503$a$-$b$ may comprise a FET stack formed in accordance with any of the embodiments discussed above with respect to FIGS. 1-13. In some embodiments, sensor 1500 may further comprise top silicon nitride 206 as is shown in FIG. 5.

In block 1402, electrode 1506 is placed in electrolyte 1505. Electrode 1506 may comprise silver or silver chloride in some embodiments. In block 1403, a gate voltage in the sub-threshold regime is applied to electrode 1506, a source voltage is applied to source 1501$a$-$b$, and a drain voltage is applied to drain 1503a-b. The drain voltage may be about 50 millivolts (mV) in some embodiments. The source, gate, and drain voltages may comprise constant voltages. The applied voltages cause a drain current to flow between source 1501a-b to drain 1503a-b, across the interface between channel 1502a-b and gate dielectric 1504.

In block 1404, a DNA strand 1509 or a biomolecule 1508 pass through nanopore 1507. A vacuum pump (not shown) may be used to force the DNA strands 1509 and/or biomolecules 1508 through nanopore 1507 in some embodiments. As DNA 1509 or biomolecules 1508 pass the channel layer 1502a-b in the nanopore 1507, the drain current in sensor 1500 changes due to the presence of DNA strand 1509 or biomolecules 1508. In block 1405, the biomolecules 1508 are detected based on the change in the drain current, or the DNA strand 1509 is sequenced based on the change in the drain current.

The technical effects and benefits of exemplary embodiments include formation of a biomolecule sensor that may also be used to sequence DNA, and does not require a coating to bind the biomolecules.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A method of forming a sensor comprising a field effect transistor (FET) sensor embedded with a nanopore, the method comprising:
   epitaxially growing a FET stack comprising a source layer including a first type of doped ions, a drain layer including a second type of doped ions matching the first type of doped ions, and a channel layer including a third type of doped ions being different from the first and second type of doped ions on a silicon on insulator (SOI) wafer to inhibit the first type of doped ions and the second type of doped ions from diffusing into the channel layer;
   forming a top silicon nitride layer over the FET stack;
   forming a bottom silicon nitride layer under the SOI wafer;
   forming a window in the bottom silicon nitride and the SOI wafer;
   forming a nanopore in the FET stack; and
   coating the nanopore with a gate dielectric to form the FET sensor.

2. The method of claim 1, wherein the channel layer has a thickness of about 3 nanometers or less.

3. The method of claim 2, wherein the channel layer has a thickness of about 1 nanometer or less.

4. The method of claim 1, wherein the drain layer and the source layer comprise heavily doped n-type silicon; and
   wherein the channel layer comprises lightly doped p-type silicon germanium or silicon carbide, and the channel layer is further doped with boron.

5. The method of claim 1, wherein the drain layer and the source layer comprise a heavily doped p-type material comprising one of silicon germanium, silicon germanium carbide, or silicon carbide, and the drain layer and source layer are further doped with boron; and
   wherein the channel layer comprises lightly doped n-type silicon.

6. The method of claim 1, wherein gate dielectric comprises a high-k dielectric material or a bilayer stack of silicon oxide (SiO2)/high-k dielectric.

7. The method of claim 1, wherein the nanopore is further formed in the top silicon nitride layer.

8. The method of claim 1, further comprising removing the top silicon nitride layer before forming the nanopore.

9. A method of forming a sensor comprising a field effect transistor (FET) sensor embedded with a nanopore, the method comprising:
   forming a silicon membrane;
   forming an oxide layer on the silicon membrane;
   forming a first metal layer on a side of the silicon membrane opposite the oxide layer to define a source region, and forming a first capping layer on top of the first metal layer;
   removing the oxide layer;
   forming a second metal layer on a side of the silicon membrane opposite the first metal layer to define a drain region such that the silicon membrane is interposed between the first metal region and the second metal region to define a channel region, and forming a second capping layer on top of the second metal layer;
   annealing the silicon membrane and first and second metal layers such that a first portion of the silicon membrane chemically reacts with the first metal layer to form a first metal silicide layer defining a source layer on a first side of the silicon membrane and a second portion of the silicon membrane chemically reacts with the second metal layer to form a second metal silicide layer defining a drain layer on a second side of the silicon membrane the channel re ion consisting of a remaining non-reacted sortion of the silicon membrane defining a channel layer;
   removing the first and second capping layers;
   forming a nanopore through the silicon membrane and the first and second metal silicide layers; and
   coating the nanopore with a gate dielectric to form the FET sensor.

10. The method of claim 9, wherein the first and second metal silicide layers comprise at least one of platinum (Pt), nickel (Ni), cobalt (Co), titanium (Ti), erbium (Er), ytterbium (Yb), or nickel platinum (NiPt).

11. The method of claim 10, wherein the first and second capping layers comprise titanium nitride or tungsten, and have a thickness of about 15 nanometers.

12. The method of claim 1, further comprising epitaxially growing a first cladding layer on the drain layer before epitaxially growing the channel layer, and epitaxially growing a second cladding layer on the channel layer before epitaxially growing the source layer, the first and second cladding layers inhibiting diffusion of the first type of doped ions and the second type of doped ions from diffusing into the channel layer.

13. The method of claim 12, wherein the first and second cladding layers are formed from a material selected from the group comprising silicon germanium (SiGe), silicon germanium doped with carbon (SiGe:C) and silicon carbide (SiC).

* * * * *